United States Patent [19]
Wilson et al.

[11] Patent Number: 4,840,562
[45] Date of Patent: Jun. 20, 1989

[54] ADJUSTABLE ORTHODONTIC BAND

[76] Inventors: Mark Wilson, 30131 Town Center Dr. #160, Laguna Niguel, Calif. 92677; Joseph Burrell, 22504 Warmside Ave., Torrance, Calif. 90505

[21] Appl. No.: 120,129

[22] Filed: Nov. 13, 1987

[51] Int. Cl.⁴ .............................................. A61C 7/00
[52] U.S. Cl. ...................................................... 433/23
[58] Field of Search ................................... 433/23, 39

[56] References Cited

U.S. PATENT DOCUMENTS 2,502,902  4/1950  Tofflemire ............................ 433/23
4,068,379  1/1978  Miller et al. ............................ 433/9

Primary Examiner—Robert Peshock
Attorney, Agent, or Firm—Gilbert Kivenson

[57] ABSTRACT

An adjustable orthodontic band incorporating a soft-metal ribbon and mechanism for independently stretching the upper and lower halves of the ribbon so as to better conform to anatomical shape of the tooth.

2 Claims, 2 Drawing Sheets

ADJUSTABLE ORTHODONTIC BAND

BACKGROUND AND OBJECTIVES

Orthodontic bands have long been used in dentistry to serve as anchoring means for archwires and other dental appliances. The primary purpose of these bands and the appliances they hold is to exert pressure through wires on misplaced or misspaced teeth. It is necessary that the bands fit snugly on the teeth to which they are attached to prevent dislodging under pressure and also to prevent accumulation of food beneath the band and the teeth. Adjustable bands to fit a variety of tooth sizes were first constructed by a French orthodontist in 1841. It was found difficult to obtain conformance to the barrel-shaped contour of many teeth when using these adjustable types; much handwork was necessary to make the band conform and it was also necessary to use large amounts of cement to fill in the areas of non-conformance between the band and the tooth to which it was attached. The adjustable band, for these reasons, gave way to the individually-fitted one. The latter is fashioned by the orthodontist from a ribbon of metal which is formed around the tooth and then welded separately. In a later development preformed bands became available. These could be adapted to individual teeth but the orthodontist needed to stock a large number of bands of differing sizes.

The adjustablility concept was however not forgotten. Boyd et al (U.S. Pat. No. 2,007,517) and Lazarus (U.S. Pat. No. 3,138,872) describe improved adjustable bands but these still require preforming of a metal strip to the approximate shape of the tooth to be banded. Again the orthodontist needs to stock a supply of band sizes and will need to do a considerable amount of fitting for each band.

It is one objective of the present invention to provide an adjustable band which automatically conforms to the shape of the tooth when it is tightened above and below the widest contour.

It is a second objective of the present invention to provide a band having a wide adaptability of differing sizes of teeth so that only two or three sizes need to be stocked. It is a third objective of the present invention to permit continuous adjustment of the band diameter during the course of the treatment to allow changes in applied force or force angle or to compensate for slippage.

These and other objectives of the present invention will be explained in the description with reference to the drawings of which the following is a listing.

DESCRIPTION OF THE INVENTION

Figure 1:
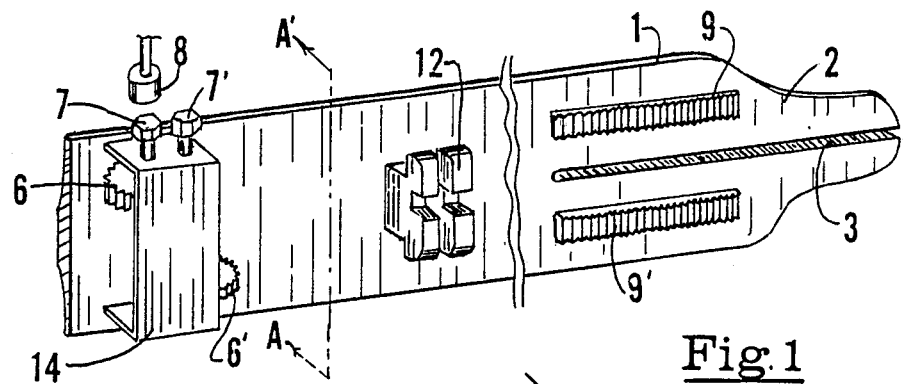
FIG. 1 is an isometric view of a band made according to the present invention showing the band tightening mechanism and an attached bracket.
Figure 2:
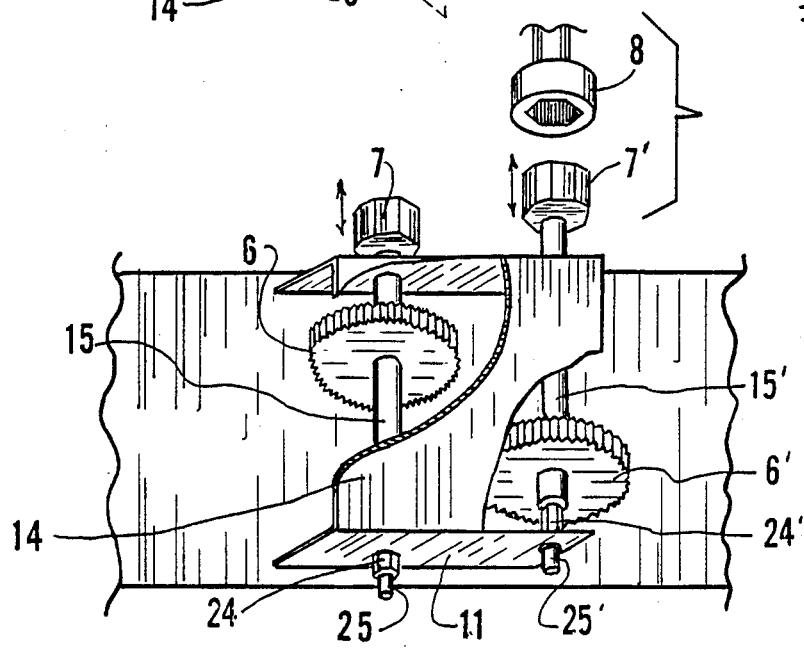
FIG. 2 is a cut-away, partial view of the band showing details of the tightening and locking mechanism.
Figure 3:
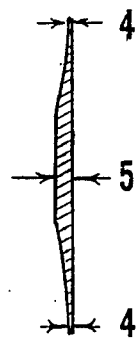
FIG. 3 is a cross section of the band taken along A-A' of FIG. 1.

The new band will be described with reference to FIGS. 1 through 4 which illustrate various features of one embodiment of the invention. The body 1 of the band is constructed of a metal which can be annealed to a "dead soft" condition. Gold and silver, for example can be used in alloys having this property. One end of the band is formed into the tang 2. A tightening assembly, shown in FIG. 2 is made up of the vertical shafts 15 and 15', the pinions 6 and 6', the driving heads 7 and 7' and the locking means 24, 24', 25 and 25'. The tightening assembly is mounted in a frame 14 which is welded or otherwise joined to the band. The racks 9 and 9' are also welded to the band as is the archwire bracket 12, FIG. 1.

Figure 4:
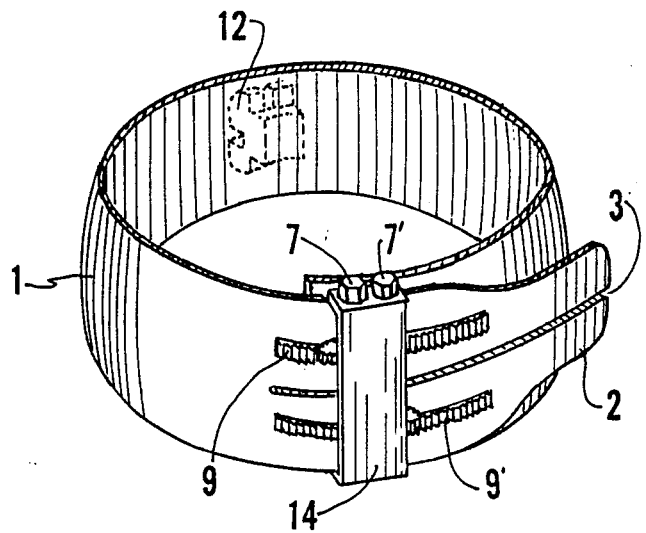
FIG. 4 is an isometric view of the band of FIG. 1 cylindrically formed and tightened as it would be around a tooth.

The band assembly is first formed into a cylindrical shape by passing tang 2 through the frame 14 until the racks 9 and 9' engage the pinions 6 and 6', respectively, FIG. 4. The drive heads 7 and 7' are raised and individually turned with tool 8 until the assembly just slips over the tooth to be banded. After the proper vertical and radial adjustments have been made, the upper and lower portions of the band are tightened by means of the driving heads 7 and 7'. As each pinion is turned, the incisal and gingival portions of the band decrease in diameter to conform to the contour of the tooth. The central portion of band also decreases in diameter but not as rapidly. The slot 3 isolates the forces being exerted in the upper and lower halves of the band so that more compliance to the shape of the tooth is achieved. This is further aided by the variation in cross section of the band, FIG. 3. The thickness of the band at the at the incisal and gingival edges is a minimum and increases to a maximum 5 near and at the tooth contour edge. A distinct advantage of the present invention over preformed bands and previously available adjustable bands is the fact that allowance for differences in incisal and gingival diameters is made automatically.

When the band is snug, the driving heads are locked. The locking method is shown in detail in FIG. 2. The drive shafts 15 and 15' pass through the hexagonal openings in the bottom plate 11 of the frame 14. Upward movement of each drive shaft frees the shaft and its pinion for turning because the lower portion of the shaft is cylindrical and smaller than the hexagonal opening. Downward movement places the hexagonal portions 24 and 24' of the drive shafts into their respective hexagonal openings thus preventing further movement of the pinions. The racks 9 and 9' are of sufficient width so that the permitted range of vertical movement of the pinions does not result in disengagement.

When the band has been properly adjusted with the bracket 12 at the desired position, the excess of tang 2 can be ground off by the orthodontist. Exposed slot area is filled in with cement. The band can be loosened or tightened for further adjustment during the course of the treatment.

In some applications the bracket 12 may be mounted on the frame 14 to minimize the number of protruding structures in the mouth.

Figure 5:
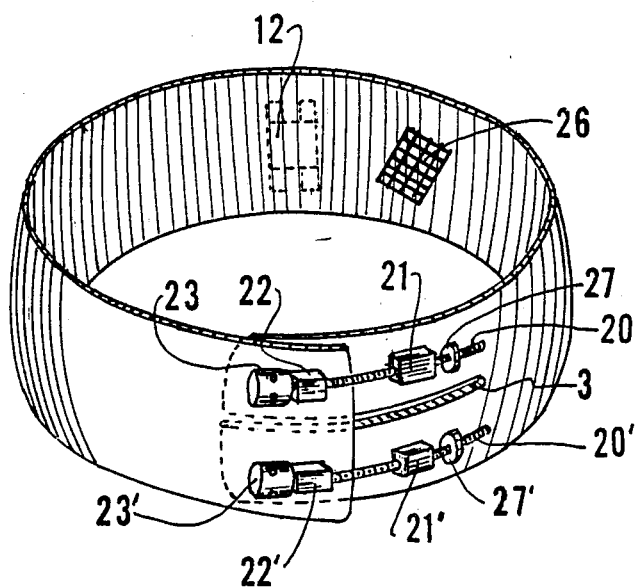
FIG. 5 is an isometric view of a second embodiment of the invention as it would be applied to a tooth.

A second embodiment of the invention is shown in FIG. 5. The tightening mechanism consists of the screws 20 and 20' interacting with the threaded stanchions 21 and 21'. The screws pass through the unthreaded bearing blocks 22 and 22' and terminate in the screw heads 23 and 23' which contain angularly spaced holes to permit the insertion of a drive pin for turning.

Lock nuts 27 and 27' are tightened to prevent subsequent loosening of the band. Excess screw length can be ground off.

In some cases additional friction between the inner surface of the band and the tooth can be achieved by welding a fine mesh 26 to the band as shown in FIG. 5.

We claim:

1. An adjustable orthodontic band comprising:
   a. a flat, soft-metal strip which is relatively thick in the center and thinning towards its edges and narrowing at one end to form a tang, said tang being split along its length into two joined halves;
   b. a pair of horizontal, gear-cut racks, one attached on the upper half and one on the lower half of the tang, the attachment being made by a suitable process such as welding;
   c. a frame attached to the other end of the strip;
   d. a pair of pinion-bearing shafts mounted to and vertically rotatable in said frame, the pinions being of a size to mesh with the gear-cut racks and capable of creating upper and lower tightening and stretching forces in the flat, soft-metal strip;
   e. locking means cooperating between the pinion-bearing shafts and said frame to inhibit rotation of the shafts when desired;
   f. a slotted bracket attached to the strip in the area between the frame and the gear-cut racks, said bracket being capable of holding archwires in an orthodontic process;

whereby the flat, soft-metal strip is first formed into a cylindrical shape by introducing the tang into said frame so that each pinion is engaged with its corresponding rack, the cylinder thus formed then being placed over a tooth to be banded, the two pinion bearing shafts unlocked and individually turned until the desired band shape and tightness are achieved and the shafts again locked, the conformance of the band to tooth shape being the result of the double stretching forces provided by the racks and pinions acting on the two halves of the soft-metal, varying thickness tang and on the non-slitted portion of the strip.

2. An adjustable band for orthodontic banding comprising:
   a. a flat, soft metal-strip split horizontally at one end;
   b. a pair of internally-threaded stanchions, one attached above and one below said split;
   c. a pair of horizontally-oriented bearing blocks, each containing a tightening screw, said blocks being attached to the unsplit end of the flat, soft-metal strip, the arrangement permitting the soft metal strip to be formed into a cylindrical shape with the tightening screws being threaded into said internally-threaded stanchions and being capable of being individually turned;
   d. stop nuts threaded on said screws;

whereby the strip is first formed into a cylindrical shape and slipped over the tooth to be banded, the screws individually tightened until a suitable conformance to the tooth shape and a suitable firmness are achieved and the stop nuts are then locked to prevent further screw turning.

* * * * *